United States Patent [19]

Moore et al.

[11] Patent Number: 4,966,678

[45] Date of Patent: Oct. 30, 1990

[54] COMPOSITIONS AND ELECTRODES COMPRISING ORGANOTIN IONOPHORES

[75] Inventors: Christopher P. Moore, Middlesex; Derek A. Thomason, Hertfordshire, both of England

[73] Assignee: Eastman Kodak Company, Rochester, N.Y.

[21] Appl. No.: 383,272

[22] Filed: Jul. 19, 1989

Related U.S. Application Data

[63] Continuation of Ser. No. 245,244, Sep. 16, 1988, abandoned.

[30] Foreign Application Priority Data

Oct. 14, 1987 [GB] United Kingdom ............... 8724049

[51] Int. Cl.⁵ ............................................. G01N 27/30
[52] U.S. Cl. ..................................... 204/418; 204/416; 524/180
[58] Field of Search ............... 204/1 T, 403, 412, 415, 204/416, 418, 430, 432, 433; 524/141, 143, 180; 252/408.1

[56] References Cited

U.S. PATENT DOCUMENTS 2,648,650  8/1953  Weinberg et al. ............... 524/180
4,020,830  5/1977  Johnson et al. ................. 204/418 X
4,115,209  9/1978  Freiser et al. .................. 204/418 X
4,237,043  12/1980  Korbanka et al. ............... 524/180
4,254,017  3/1981  Dworkin et al. ................. 524/180
4,285,856  8/1981  Wehner et al. .................. 524/180 X
4,505,800  3/1985  Toner et al. .................... 204/418

OTHER PUBLICATIONS

Wuthier et al., Helvetica Chimica Acta, vol. 68, pp. 1822-1827, 1985.

Primary Examiner—Nam X. Nguyen
Attorney, Agent, or Firm—John R. Everett

[57] ABSTRACT

An ion-sensitive composition and an ion-selective electrode is disclosed in which the ionophore is an organotin having the formula $$R_x^1 Sn(SR^2)_{4-x}$$

or $$R_y^1 Sn(SR^3 - X - R^3 S)_{4-y} SnR^1$$

wherein
x is 0 or an integer from 1 to 3;
y is 2 or 3;
each $R^1$ independently is substituted or unsubstituted alkyl or substituted or unsubstituted aryl;
each $R^2$ independently is substituted or unsubstituted alkyl.
each $R^3$ independently is substituted or unsubstituted alkylene; and,
X is a single chemical bond or a linking group.

14 Claims, 1 Drawing Sheet

COMPOSITIONS AND ELECTRODES COMPRISING ORGANOTIN IONOPHORES

This is a continuation of application Ser. No. 245,244, filed Sept. 16, 1988, now abandoned.

FIELD OF THE INVENTION

The present invention relates to the use of certain organotin anionic ionophores, compositions and to electrodes comprising such ionophore compositions.

BACKGROUND OF THE INVENTION

An ionophore is a compound which is capable of forming a complex with an ion. The organotin compounds used in the present invention are anionic ionophores i.e. they are capable of forming a complex with an anion. The complex may be formed by contacting the anionic ionophore with a solution containing one or more anions. The formation of such complexes finds use in a wide variety of applications. For example, the complex forming reaction may be utilised in a method for determining ion concentration.

There are many situations in which the ability to determine the activities of ions in fluids would be beneficial. One method of ion measurement involves the use of ion sensitive electrode potentiometry. The use of ion selective electrodes and related sensors depends on the measurement of membrane potentials which arise as a result of the partition of ions between an ion selective membrane and aqueous phases. These potentials cannot be measured independently, but can be deduced from the voltage generated by a complete electrochemical cell comprising an ion selective electrode and a reference electrode.

Tri-n-alkyl tin halides and related compounds have been described as anion carriers in U. Wuthier et al, Anal. Chem., 1984, 56, 535 and U. Wuthier et al, Helv. Chim. Acta., 1985, 68, 1822. These papers describe the incorporation of the compounds in solvent polymeric membranes of anion selective electrodes. A disadvantage of these compounds is that they are hydrolytically unstable and readily decompose under basic conditions.

SUMMARY OF THE INVENTION

This invention provides an ion sensitive composition comprising an alkylthio substituted organotin ionophore, a compound capable of solvating the ionophore and a supporting matrix.

The alkylthio substituted organotin ionophores have the formula:

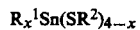

or

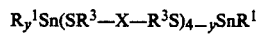

wherein
X is 0 or an integer from 1 to 3;
y is 2 or 3;
each $R^1$ independently is substituted or unsubstituted alkyl or substituted or unsubstituted aryl;
each $R^2$ independently is substituted or unsubstituted alkyl.
each $R^3$ independently is substituted or unsubstituted alkylene; and,
X is a single chemical bond or a linking group.

An advantage of these ionophores is that they are hydrolytically and alkali stable. Also, they retain the advantages of being easy to prepare, very soluble in organic solvents and have low solubility in water.

In one aspect of the invention there is provided a method of forming an anion complex comprising the step of contacting in solution an anion with an anionic ionophore characterised in that the anionic ionophore is an organotin compound as defined above.

In a preferred aspect there is provided an ion sensitive electrode having an ion sensitive membrane comprising an ionophore as defined above.

Preferred organotin compounds having the formulae defined above are those wherein each tin atom has one or three alkylthio substituents i.e. x is 1 or 3 and y is 3.

Preferably, each $R^1$ independently represents substituted or unsubstituted alkyl having from 1 to 12 carbon atoms e.g. methyl, ethyl, propyl, butyl, octyl, dodecyl and acetoxypropyl, or substituted or unsubstituted phenyl.

Preferably, each $R^2$ independently represents substituted or unsubstituted alkyl having from 1 to 12 carbon atoms. More preferably, each alkyl group is substituted with one or more functional groups. Such functional groups may beneficially contain atoms having an electropositive character.

In a particularly preferred embodiment, $R^2$ is represented by the formula $-(CH_2)_pZ$ wherein p is an integer from 1 to 6 and Z is a functional group. Suitable functional groups include $-OH$, $-NH_2$, $-OCOR$, $-NHCOR$, $-NHPO(OR)_2$, $-COR$, $-COOR$, $-SO_2R$ and $-OSiR_3$ wherein R represents substituted or unsubstituted alkyl or aryl wherein the substituent is an electron-withdrawing group.

Preferably, each $R^3$ independently is an optionally substituted alkylene group having from 1 to 12, more preferably from 1 to 6, most preferably from 1 to 3 carbon atoms.

X is a linking group such as a single chemical bond or the residue of a dicarboxylic acid e.g. malonate, phthalate and phthalamide.

DESCRIPTION OF THE DRAWING

In the accompanying drawing.

DETAILS OF THE INVENTION

Figure 1:
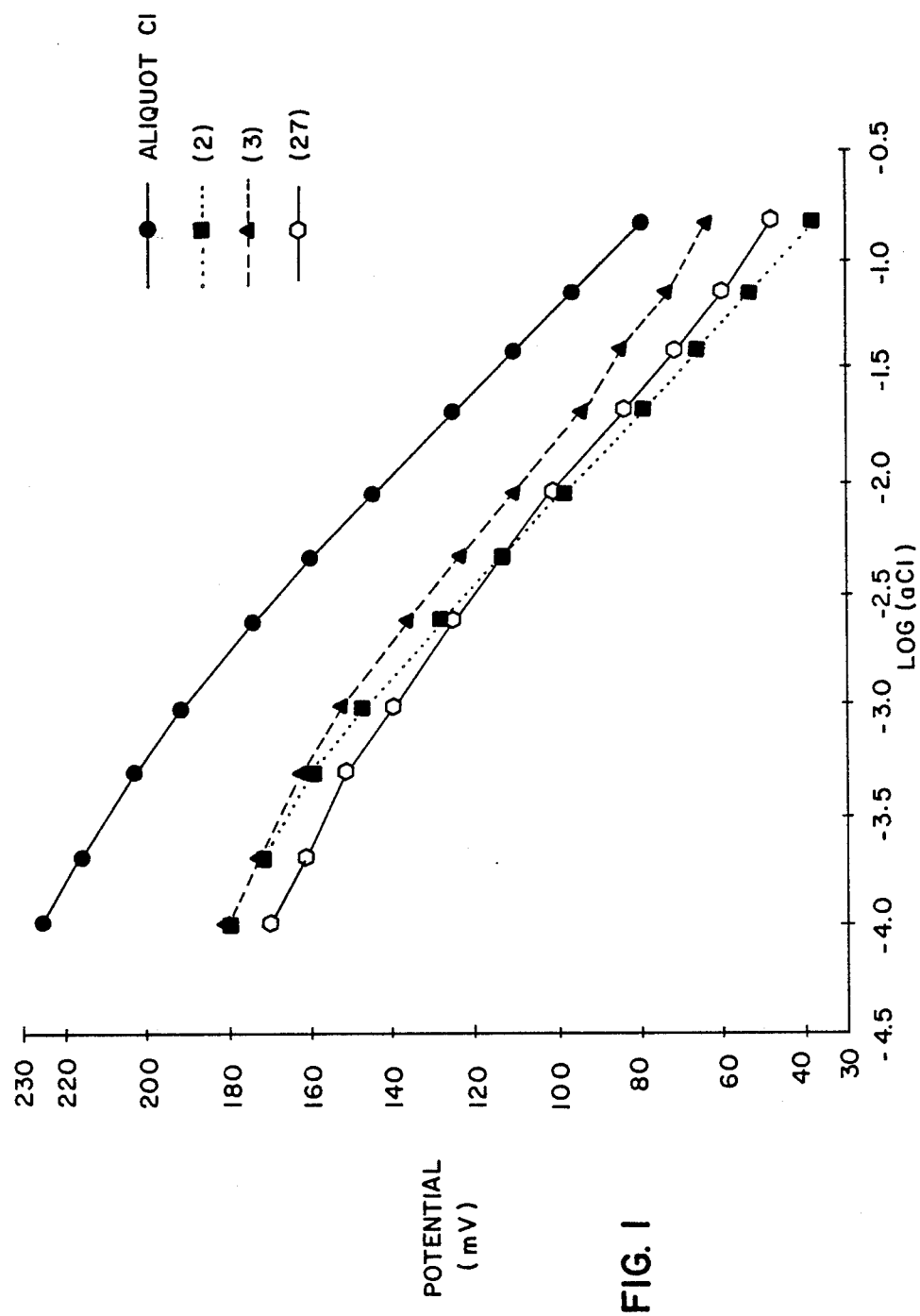
FIG. 1 shows the response characteristics of three chloride ion sensitive electrodes according to the invention and an electrode wherein the ionophore is an ammonium salt.

Specific examples of the organotin ionophores are as follows:
1. $(n-C_4H_9)_3SnS(CH_2)_{11}CH_3$
2. $(n-C_4H_9)_3SnS(n-C_4H_9)$
3. $(n-C_4H_9)_3SnS(CH_2)_2COOCH_3$
4. $(n-C_4H_9)_3SnSCH_2COOCH_3$
5. $(n-C_4H_9)_2SnS(CH_2)_2COCH_3$
6. $(n-C_4H_9)_3SnS(CH_2)_2SO_2CH_3$
7. $(n-C_4H_9)_3SnSCH_2CH_2OCOCH_3$
8. $(n-C_4H_9)_3SnS(CH_2)_2OOCCH_2COO(CH_2)_2SSn(n-C_4H_9)_3$
9. $(n-C_4H_9)_3SnSCH_2(CHOH)CH_2OH$
10. $(n-C_4H_9)_3SnS(CH_2)_2OSi(CH_3)_2(t-C_4H_9)$
11. $(n-C_4H_9)_3SnS(CH_2)_2NH_2$
12. $(n-C_4H_9)_3SnS(CH_2)_2NHCOCF_3$
13. $(n-C_4H_9)_3SnS(CH_2)_2NHCOCH_3$
14.

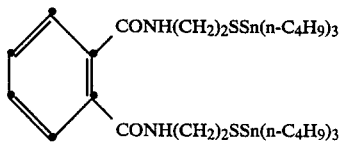

15. (n—$C_4H_9$)$_3$SnS(CH$_2$)$_3$SSn(n—$C_4H_9$)$_3$
16. (n—$C_4H_9$)$_3$SnS(CH$_2$)$_6$SSn(n—$C_4H_9$)$_3$
17. (n—$C_4H_9$)$_3$SnS(CH$_2$)$_9$SSn(n—$C_4H_9$)$_3$
18. (n—$C_8H_{17}$)$_3$SnS(CH$_2$)$_{11}$CH$_3$
19. (n—$C_{12}H_{25}$)$_3$SnS(CH$_2$)$_{11}$CH$_3$
20. ($C_6H_5$)$_3$SnS(CH$_2$)$_{11}$CH$_3$
21. (n—$C_4H_9$)$_2$Sn[S(CH$_2$)$_{11}$CH$_3$]$_2$
22. (n—$C_4H_9$)$_2$Sn[S(CH$_2$)$_2$COOCH$_3$]$_2$
23.

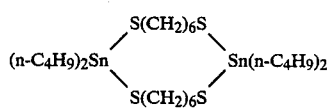

24. n—$C_4H_9$Sn[S(CH$_2$)$_{11}$CH$_3$]$_3$
25. n—$C_4H_9$Sn[S(CH$_2$)$_2$OH]$_3$
26. n—$C_4H_9$Sn[S(CH$_2$)$_2$OCOCH$_3$]$_3$
27. n—$C_4H_9$Sn[S(CH$_2$)$_2$COOCH$_3$]$_3$
28. n—$C_4H_9$SN(SCH$_2$COOCH$_3$)$_3$
29. Sn[S(CH$_2$)$_2$COOCH$_3$]$_4$
30. [CH$_3$COO(CH$_2$)$_3$]$_3$SnS(n—$C_4H_9$)
31. [CH$_3$COO(CH$_2$)$_2$]$_3$SnS(CH$_2$)$_2$COOCH$_3$
32. (n—$C_4H_9$)$_3$SnS(CH$_2$)$_3$OCOCH$_3$
33. (n—$C_4H_9$)$_3$SnS(CH$_2$)$_3$OH
34. n—$C_4H_9$Sn(SC$_4H_9$—n)$_3$
35. (n—$C_4H_9$)$_3$SnS(CH$_2$)$_2$NHPO(OC$_2H_5$)$_2$
36. (n—$C_4H_9$)$_3$SnS(CH$_2$)$_2$OH

Many of the ionophores may be prepared by reaction of an appropriate tin halide with an appropriate thiol, e.g.,

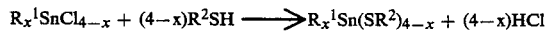

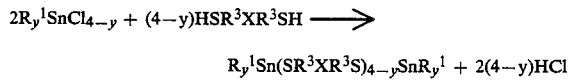

The ionophores may also be made by the procedures disclosed in U.S. Pat. No. 2,648,650.

Specific examples of the preparation of organotin ionophores used in the invention are as follows:

Preparation of alkylthioalkyltins (1), (16), (17), (22)', (24)*, (23)

The appropriate tin halide (10 mmol) was suspended in water (10 ml) and the appropriate thiol (10 mmol) was added to it. Aqueous sodium hydroxide (10 mmol, 400mg in 5 ml) was added dropwise and the mixture was stirred for 24–48 hours, by which time a heavy oil had separated. For bisthiols and tin dichloride and trichloride a higher number of equivalents of the appropriate reagent was used. The oil was separated and the aqueous phase was extracted with ether (3×20 ml); the combined organic phases were dried, evaporated and the residue was generally purified by column chromatography; in some instances excess unreacted thiol was removed by distillation under reduced pressure. All spectroscopic and analytical data were consistent with the proposed structures.

Modifications to the above method made with regard to compounds (22) and (24) are as follows:
' sodium bicarbonate used as base;
* potassium carbonate used as base, acetone used as solvent.

Preparation of Alkylthioalkyl and aryltins (2), (3), (18), (19), (20), (27)

The tin halide (10 mmol) was dissolved in toluene (50 ml) or THF (50 ml); triethylamine (10 mmol, 1.01g, 1.39 ml) was added, followed by the thiol (10 mmol). After the initial precipitation had finished the mixture was heated to reflux overnight (16 h). After removal of the solvent the residue was partitioned between water (50 ml) and ether (50 ml). The aqueous phase was separated and extracted with ether (2×30 ml); the combined organic phases were washed with hydrochloric acid (2%, 50 ml) and water (50 ml), dried and evaporated to leave the crude product as an oil which was purified by column chromatography. In some instances excess unreacted thiol was removed by distillation under reduced pressure. All spectroscopic and analytical data were consistent with the proposed structures.

Preparation of di-n-butylbis-n-dodecylthiotin (21)

This compound was prepared from di-n-butyltin-oxide and 1 dodecanethiol by azeotropic removal of water using the method described in U.S. Pat. No. 2,648,650. All spectroscopic and analytical data were consistent with the proposed structure.

Preparation of Alkylthiotri-n-butyltins (9), (11), (4)

Bis(tri-n-butyltin)oxide (10 mmol, 5.79 g) was dissolved in toluene (50 ml), and the appropriate thiol (5 mmol) was added. The mixture was heated to reflux for 16 h using either anhydrous magnesium sulphate or molecular sieves to remove the water formed during the course of the reaction. The mixture was filtered and evaporated to leave essentially pure product as a colourless oil. Residual contaminating thiol was removed by high vacuum treatment, or by brief column chromatography. All spectroscptic and analytical data were consistent with the proposed structures.

Preparation of (3-Oxo-1-butylthio)tri-n-butyltin (5)

Thiolacetic acid (333 mmol, 25.34 g) was dissolved in toluene (200 ml) and the solution added to a solution of 3-buten-2-one (333 mmol, 23.33 g) in toluene (100 ml), containing benzoyl peroxide (0.33 mmol, 81 mg). The mixture was stirred at 22° C. for 2 h, by which time TLC indicated the reaction was complete. The solvent was removed to leave the crude product as a malodorous yellow oil (42.48 g). A sample (20 g) was purified by column chromatography to leave 1-thioacetoxy-3--butanone as a colourless oil (12.42 g, 54%). The oil (25 mmol, 3.65 g) and bis(tri-n-butyltin)oxide (12.5 mmol, 7.45 g) were dissolved in toluene (100 ml) and the mixture was heated to reflux for 24 h. The solvent was removed to leave a waxy solid which was purified by column chromatography to leave the product as a colourless oil (2.94 g, 25%). Higher yields may be obtained by using 2 equivalents of the tin oxide. All spectroscopic and analytical data were consistent with the proposed structures.

Preparation of (2-Methanesulphonyl-1-ethylthio)tri-n-butyltin (6)

This compound was prepared analogously to (5), starting from thiolacetic acid and methylvinylsulphone, leading to the intermediate sulphone (47%), treating subsequently with the tin oxide to give the required product (6) (41%). All spectroscopic and analytical data were consistent with the proposed structures.

Preparation of (t-Butyldimethylsilyloxyalkylthio)tri-n-butyltin (10)

This compound was prepared with t-butylchlorodimethylsilane from the appropriate alcohol using a standard silylation procedure. All spectroscopic and analytical data were consistent with the proposed structure.

Preparation of Bis[2-(tri-n-butyltinthio)ethyl]malonate (8)

(2-Hydroxyethylthio)tri-n-butyltin (24 mmol, 8.8 g) was dissolved in anhydrous toluene (80 ml). Sodium hydride (90%, 24 mmol, 640 mg) was added and the mixture was heated to reflux for 1.5 h during which time the sodium salt was formed. A solution of malonyl dichloride (12 mmol, 1.69 g) in anhydrous toluene (5 ml), was added dropwise at 22°, and then the mixture was heated to reflux for 16 h. The cooled solution was diluted with water (50 ml) and the organic phase was separated; the aqueous phase was extracted with ether (2×30 ml) and the combined organic phases were washed with water (50 ml), dried and evaporated to leave the product as an orange oil which was purified by column chromatography. Pure (8) was obtained as a colourless oil (3.26 g, 34%). All spectroscopic and analytical data were consistent with the proposed structure.

Preparation of (2-Acetamidoethylthio)tri-n-butyltin (13)

(2-Aminoethylthio)tri-n-butyltin (6.8 mmol, 2.5 g) and triethylamine (6.8 mmol, 687 mg) were dissolved in THF (75 ml). This mixture was cooled to 0° C. and acetyl chloride was added dropwise, and the resultant mixture stirred at 22° C. for 16 h. The solvent was evaporated, the residue was suspended in ether (50 ml), and the precipitated triethylamine hydrochloride was removed by filtration. The salt was washed with ether (20 ml), and the combined organic phases were washed with water (25 ml), dried and evaporated to leave the crude product which was purified by column chromatography leaving the pure amide (13) as a colourless oil (2.35 g, 85%). All spectroscopic and analytical data were consistent with the proposed structure.

Preparation of Tetrakis(2-methoxycarbonylethylthio)tin (29)

Methyl-3-mercaptopropionate (48 mmol, 5.76 g) was dissolved in anhydrous toluene (75 ml) under nitrogen, and heated to 90° C. A solution of tin(IV) chloride in dichloromethane (1M, 12 mmol, 12 ml) was added dropwise over 1.5 h, and then the reaction was maintained at 90° C. for a further 48 h, until hydrogen chloride evolution finished. The mixture was then filtered to remove by products and evaporated to leave the product as a pale yellow oil (6.64 g, 93%).

The ion sensitive composition of the invention may be used in the form of a membrane in an ion sensitive electrode. A variety of ion sensitive electrodes having an ion sensitive polymeric membrane are known.

For example, electrodes wherein the membrane separates a solution to be tested From an internal reference solution are widely used. Such a membrane may comprise the ionophore, a supporting matrix e.g. poly(vinyl chloride) and a compound capable of solvating the ionophore e.g. a hydrophobic carrier solvent. The ionophore must be capable of sequentially complexing the desired ion, transporting the ion through the membrane and releasing the ion.

Electrochemical sensors comprising an electrode body having an ion sensitive polymeric membrane coated thereon are also well known.

One such type of membrane electrode is commonly referred to as a coated wire electrode. Such an electrode may comprise a molecular dispersion or a solution of an ionophore supported on a metal wire by a polymer matrix. The composition of this membrane may be identical to that of the membranes described above but the membrane does not have to meet the requirement of being self supporting. Coated wire electrodes have been extensively described in the literature e.g. U.S. Pat. No. 4,115,209.

Another type of electrode having an ion sensitive membrane coated thereon relies on the effect of the electric field in the vicinity of the membrane. For example, U.S. Pat. No. 4,020,830 describes a chemical sensitive field effect transistor transducer capable of selectively detecting and measuring chemical properties of substances to which the transducer is exposed. Also, International Publication No. WO 87/01454 describes an ion sensitive field effect transistor (ISFET) having a polymeric membrane containing ion exchange sites. ISFETS can be made wherein the ion sensitive membrane comprises an organotin ionophore in a polymer matrix. In such an electrode, it is not necessary for the ionophore to be able to carry the captured ion across the membrane.

Membrane electrodes constructed from poly(vinyl chloride) which incorporate the organotin compounds have been shown to exhibit response characteristics approaching those predicted by the Nernst equation when evaluated in solutions containing varying activities of chloride ions. Furthermore, some of these materials have exhibited deviations from the theoretical selectivity sequence predicted by the Hofmeister Series, especially with regard to the selectivity of chloride versus nitrate. The theoretical selectivity sequence for anion sensitive electrodes based on ion exchange species e.g. quaternary ammonium salts is represented by the Hofmeister Series as follows:

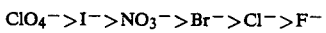

$ClO_4^- > I^- > NO_3^- > Br^- > Cl^- > F^-$

Binders for use in the ion selective membrane of the instant invention include any of the hydrophobic natural or synthetic polymers capable of forming thin films of sufficient permeability to produce in combination with the ionophores and ionophore solvent(s) apparent ionic mobility across the membrane. Specifically, polyvinyl chloride, vinylidene chloride, acrylonitrile, polyurethanes (particularly aromatic polyurethanes), copolymers of polyvinyl chloride and polyvinylidene chloride, polyvinyl butyral, polyvinyl formal, polyvinylacetate, silicone elastomers, and copolymers of polyvinyl alcohol, cellulose esters, polycarbonates, carboxylated polymers of polyvinyl chloride and mixtures and copolymers of such materials have been found useful. Films of such materials which include the ionophores and carrier solvents may be prepared using conventional film coating or casting techniques and may be formed either by coating and film formation directly over the internal reference electrode or some suitable interlayer or by formation separately and lamination thereto.

For certain electrodes, the membrane requires a carrier solvent. The carrier solvent provides ion mobility in the membrane and, although the ion transfer mechanism within such membrane is not completely understood, the presence of a carrier solvent is apparently necessary to obtain good ion transfer.

The carrier solvent must, of course, be compatible with the membrane binder and be a solvent for the carrier. Two other characteristics are most desirable. One is that the carrier solvent be sufficiently hydrophilic to permit rapid wetting of the membrane by an aqueous sample applied thereto to permit ionic mobility across the interface between the sample and the membrane. Alternatively, the carrier must be rendered hydrophilic by the action of a suitable noninterfering surfactant which improves contact between the sample in contact with the membrane and the carrier.

The other highly desirable characteristic is that the carrier solvent be sufficiently insoluble in water that it does not migrate significantly into an aqueous sample contacted with the surface of the membrane as described hereinafter. Generally, an upper solubility limit in water would be about $10^{-3}$M/l. Within these limits, substantially any solvent for the ionophore which is also compatible with the binder may be used. As mentioned above, it is, of course, preferred that the solvent also be a plasticizer for the binder. It is also desirable that the ion carrier solvent be substantially non volatile to provide extended shelf life for the electrode. Among the useful solvents are phthalates, sebacates, aromatic and aliphatic ethers, phosphates, mixed aromatic aliphatic phosphates, adipates, and mixtures thereof.

The ion selective membranes contain the described components over a wide range of concentrations and coverages. The membrane may contain the ionophore in an amount from 1 to 65 percent by weight, preferably, the ionophore is present in an amount from 20 to 50 percent by weight. In general, it is essential to employ the ionophore in the least amount necessary to provide the required response. The coverage of the ionophore depends upon the compound used to solvate it, as well as other factors. Some membranes comprise a hydrophobic binder having the solvent and ionophore dispersed therein.

The carrier solvent is present in an amount sufficient to solvate the ionophore. The amount therefore depends on the particular solvent and ionophore chosen. More solvent may be used than is necessary to solvate the ionophore so that it remains solvated under a variety of storage conditions.

The amount of hydrophobic binder which is present is determined by the desired thickness of the membrane and by the necessity for providing support for the ionophore solvent dispersion. The thickness of the membrane will depend on the type of electrode in which it is used. For example, the preferred thickness of a self supporting membrane used to separate two solutions may be in the range from 0.1 to 0.5 mm whereas the preferred thickness of a membrane on a field effect transistor transducer may be in the range from 2 to 50μm.

The ion selectivity of membrane electrodes can be observed by measuring the steady state difference in electrical potential between solution 1 and solution 2 (both usually aqueous) in the cell arrangement schematically represented by the following:

Reference electrode 1/solution 1//
membrane//solution 2/reference electrode 2.

The calculations required to determine the ionic activity of solution 2 (generally the solution of unknown concentration) are derived from the well known Nernst equation.

The electrode of the invention may incorporate an integral reference electrode. In this embodiment the electrode includes within its structure substantially all of the components needed for making a potentiometric determination with the exception of a second reference electrode, the potential indicating device and associated wiring so that in use the user merely needs to provide for contacting the sample with the ion selective membrane, e.g. by application of a small quantity of the sample to be analyzed (in the order of $<50$ μl) thereto and making the necessary electrical connections. Automated dispensers for applying controlled amounts of sample to the electrode at the appropriate location are known and any such dispenser, or for that matter careful manual dispensing, may be used to contact the sample with the electrode. Alternatively, the electrode may actually be immersed in or contacted with the surface of the solution under analysis.

Reference electrodes such as silver/silver chloride and saturated calomel electrodes for use in combination with the electrodes of the present invention are also well known.

Similarly, potentiometers capable of reading the potentials generated in the ion selective electrodes of the present invention are well known and can be used to give an indication of the potential from which the ionic activity in the unknown solution may be calculated.

By incorporating computing capability into the potentiometric device it is, of course, possible to obtain direct readings of specific ionic concentrations in solution as a function of ionic activity.

The invention is further illustrated with reference to the following Example.

EXAMPLE

A number of organotin compounds were tested by incorporating them as the ionophore in a membrane electrode and evaluating the electrode response to chloride ion in solution.

In fabricating the electrode membranes, a constant weight/weight ratio of poly(vinyl chloride) to tricresyl phosphate plasticizer (2:3) was maintained for all membranes, the weight of the ionophore under test being varied from 5 to 65% by weight of the total. A disc cut from each master membrane was attached to the end of PVC tubing using a PVC/plasticizer mixture dispersed in tetrahydrofuran (THF). A glass tube was inserted within the PVC tube so that the membrane covered the opening at the end of the glass tube. The electrode was completed by the addition of an internal Filling solution (0.1M NaCl) and a silver/silver chloride reference element.

The evaluation of electrode response was assessed by using a modified Radiometer D470 titration system and a remote silver/silver chloride reference electrode with an ammonium nitrate salt bridge. This system uses a known addition technique and provides information on linear range, slope, limit of detection and selectivity coefficients. As a comparison, the response characteristics of methyltri-n-octyl ammonium chloride (Aliquat Cl) have also been assessed.

As shown by the results presented in FIG. 1, electrodes based on compounds (2), (3) and (27) exhibited response characteristics that approach those predicted by the Nernst equation.

Having regard to selectivity, the results obtained for the comparison electrode based on methyltri-n-octyl ammonium chloride exhibited the selectivity series predicted by the Hofmeister series. While this selectivity series is retained in electrodes based on compound (27), deviations from this series are exhibited by compounds (Z) and (3), especially with regard to the selectivity for chloride in the presence of nitrate and, to a lesser extent, perchlorate. In the case of nitrate, both compounds show an improvement in selectivity of between 2 and 3 orders of magnitude compared to the quaternary ammonium salt.

Other organotin compounds tested which provided electrodes exhibiting response characteristics that approach those predicted by the Nernst equation are as follows: (1), (4), (5), (6), (7), (11), (12), (32) and (36).

The invention has been described in detail with particular reference to preferred embodiments thereof, but it will be understood that variations and modifications can be effected within the spirit and scope of the invention.

What is claimed is:

1. An ion sensitive electrode having an ion-sensitive membrane comprising an alkylthio substituted organotin having the following formula:

$$R^1_x Sn(SR^2)_{4-x}$$

or $$R^1_y Sn(SR^3-X-R^3S)_{4-y} SnR^1$$

wherein
x is 0 or an integer from 1 to 3;
y is 2 or 3;
each $R^1$ independently is substituted or unsubstituted alkyl or substituted or unsubstituted aryl;
each $R^2$ independently is substituted or unsubstituted alkyl.
each $R^3$ independently is substituted or unsubstituted alkylene; and,
X is a single chemical bond or a linking group.

2. An electrode according to claim 1 wherein x is 1 or 3 and y is 3.

3. An electrode according to claim 1 or claim 2 wherein each $R^1$ independently represents substituted or unsubstituted alkyl having from 1 to phenyl.

4. An electrode according to claims 1, 2, 3 wherein each $R^2$ independently represents substituted or unsubstituted alkyl having from 1 to 12 carbon atoms.

5. An electrode according to claims 1, 2, 3 wherein $R^2$ is represented by the formula $-(CH_2)_p Z$ wherein p is an integer from 1 to 6 and Z is a functional group.

6. An electrode according to claim 5 wherein the functional group is $-OH$, $-NH_2$, $-OCOR$, $-NHCOR$, $-NHPO(OR)_2$, $-COR$, $-COOR$, $-SO_2R$ or $-OSiR_3$ and R represents alkyl or aryl optionally substituted with an electron withdrawing substituent.

7. An electrode according to claims 1, 2 or 3 wherein each $R^3$ independently is an optionally substituted alkylene group having from 1 to 6 carbon atoms.

8. An electrode according to claim 7 wherein X is the residue of a dicarboxylic acid.

9. An ion-sensitive composition comprising
(a) from 1 to 65% by weight of an alkylthio-substituted organotin ionophore having the formula $$R^1_x Sn(SR^2)_{4-x}$$

$$R^1_y Sn(SR^3-X-R^3S)_{4-y} SnR^1$$

wherein
x is 0 or an integer from 1 to 3;
y is 2 or 3;
each $R^1$ independently is substituted or unsubstituted alkyl or substituted or unsubstituted aryl;
each $R^2$ independently is substituted or unsubstituted alkyl;
each $R^3$ independently is substituted or unsubstituted alkylene; and
X is a single chemical bond or a linking group; and
(b) a compound capable of solvating the ionophore in a support matrix wherein such compounds are selected from the group consisting of phthalates, sebacates, phosphate, mix aromatic aliphatic phosphates, adipates and mixtures thereof.

10. An ion-sensitive composition comprising from 1 to 65% by weight of an ionophore, a compound capable of solvating the ionophore and a support matrix; wherein the ionophore is an alkylthio-substituted organotin compound having the formula:

$$R^1_x Sn(SR^2)_{4-x}$$

or $$R^1_y Sn(SR^3-X-R^3S)_{4-y} SnR^1$$

in which
x is 0 or an integer from 1 to 3;
y is 2 or 3;
each $R^1$ independently is unsubstituted alkyl or substituted or unsubstituted aryl;
each $R^2$ independently is substitued or unsubstituted alkyl;
each $R^3$ independently is substituted or unsubstituted alkylene; and
X is a single chemical bond or a linking group.

11. The ion-sensitive composition of claim 10 wherein the ionophore is selected from the group consisting of:
(n—$C_4H_9$)$_3$SnS(CH$_2$)$_{11}$CH$_3$;
(n—$C_4H_9$)$_3$SnS(n—$C_4H_9$);
(n—$C_4H_9$)$_3$SnS(CH$_2$)$_2$COOCH$_3$;
(n—$C_4H_9$)$_3$SnSCH$_2$COOCH$_3$;
(n—$C_4H_9$)$_3$SnS(CH$_2$)$_2$COCH$_3$;
(n—$C_4H_9$)$_3$SnS(CH$_2$)$_2$SO$_2$CH$_3$;
(n—$C_4H_9$)$_3$SnSCH$_2$CH$_2$OCOCH$_3$;
(n—$C_4H_9$)$_3$SnS(CH$_2$)$_2$OOCCH$_2$COO(CH$_2$)$_2$SSn-(n—$C_4H_9$)$_3$;
(n—$C_4H_9$)$_3$SnSCH$_2$(CHOH)CH$_2$OH;
(n—$C_4H_9$)$_3$SnS(CH$_2$)$_2$OSi(CH$_3$)$_2$(t—$C_4H_9$);
(n—$C_4H_9$)$_3$SnS(CH$_2$)$_2$NH$_2$;
(n—$C_4H_9$)$_3$SnS(CH$_2$)$_2$NCHOCF$_3$;
(n—$C_4H_9$)$_3$SnS(CH$_2$)$_2$NHCOCH$_3$;

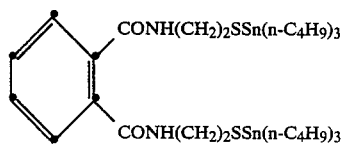

$(n-C_4H_9)_3SnS(CH_2)_3SSn(n-C_4H_9)_3$;
$(n-C_4H_9)_3SnS(CH_2)_6SSn(n-C_4H_9)_3$;
$(n-C_4H_9)_3SnS(CH_2)_9SSn(n-C_4H_9)_3$;
$(n-C_8H_{17})_3SnS(CH_2)_{11}CH_3$;
$(n-C_{12}H_{25})_3SnS(CH_2)_{11}CH_3$;
$(C_6H_5)_3SnS(CH_2)_{11}CH_3$;
$(n-C_4H_9)_2Sn[S(CH_2)_{11}CH_3]_2$;
$(n-C_4H_9)_2Sn[S(CH_2)_2COOCH_3]_2$;

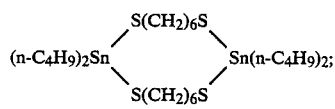

$n-C_4H_9Sn[S(CH_2)_{11}CH_3]_3$;
$n-C_4H_9Sn[S(CH_2)_2OH]_3$;
$n-C_4H_9Sn[S(CH_2)_2OCOCH_3]_3$;
$n-C_4H_9Sn[S(CH_2)_2COOCH_3]_3$;
$n-C_4H_9Sn(SCH_2COOCH_3)_3$;
$Sn[S(CH_2)_2COOCH_3]_4$;
$[CH_3COO(CH_2)_3]_3SnS(n-C_4H_9)$;
$[CH_3COO(CH_2)_3]_3SnS(CH_2)_2COOCH_3$;
$(n-C_4H_9)_3SnS(CH_2)_3OCOCH_3$;
$(n-C_4H_9)_3SnS(CH_2)_3OH$;
$n-C_4H_9Sn(SC_4H_9-n)_3$;
$(n-C_4H_9)_3SnS(CH_2)_2NHPO(OC_2H_5)_2$; or
$(n-C_4H_9)_3SnS(CH_2)_2OH$.

12. An ion-sensitive composition according to claims 9 or 10 wherein X is 1 or 3 and Y is 3.

13. An ion-sensitive composition according to claims 9 or 10 wherein each $R^1$ independently represents an unsubstituted alkyl having from 1 to 12 carbon atoms or substituted or unsubstituted phenyl.

14. The ion sensitive composition of claim 9 or 10 wherein the ionophore is present in an amount of 20 to 50% by weight.

* * * * *

UNITED STATES PATENT OFFICE
CERTIFICATE OF CORRECTION

PATENT NO. : 4,966,678

DATED : October 30, 1990

INVENTOR(S) : Christopher P. Moore et al

It is certified that error appears in the above-identified patent and that said Letters Patent is hereby corrected as shown below:

Col. 9, line 59, the part reading
"from 1 to phenyl."
should read
--from 1 to 12 carbon atoms or substituted or unsubstituted phenyl.--;

Col. 9, line 63, the part reading
"claims 1, 2, 3"
should read
--claims 1, 2, 3 or 4--;

Col. 10, line 5, the part reading
"carbon , atoms."
should read
--carbon atoms.--; and

UNITED STATES PATENT AND TRADEMARK OFFICE
CERTIFICATE OF CORRECTION

PATENT NO. : 4,966,678

DATED : October 30, 1990

INVENTOR(S) : Christopher P. Moore et al.

It is certified that error appears in the above-identified patent and that said Letters Patent is hereby corrected as shown below:

Col. 10, line 67, the part reading
"$(n-C_4H_9)_3SnS(CH_2)_2NCHOCF_3;$"

should read
--$(n-C_4H_9)_3SnS(CH_2)_2NHCOCF_3;$--.

Signed and Sealed this

Third Day of March, 1992

Attest:

HARRY F. MANBECK, JR.

*Attesting Officer*     *Commissioner of Patents and Trademarks*